United States Patent
Lanos et al.

(10) Patent No.: US 9,857,355 B2
(45) Date of Patent: *Jan. 2, 2018

(54) BIOLOGICAL ASSAY OF PEPTIDOGLYCANS

(71) Applicant: ROQUETTE FRERES, Lestrem (FR)

(72) Inventors: Pierre Lanos, La Bassee (FR); Marc Biguet, Neuve Chapelle (FR); Roselyne Bernard, Lestrem (FR); Fabrice Allain, Lille (FR); Mathieu Carpentier, Saint Andre lez Lille (FR); Agnès Denys, Lille (FR); Héla Hacine-Gherbi, Villeneuve d'Ascq (FR)

(73) Assignee: Roquette Freres, Lestrem (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/779,353

(22) PCT Filed: Mar. 25, 2014

(86) PCT No.: PCT/EP2014/055888
§ 371 (c)(1),
(2) Date: Sep. 23, 2015

(87) PCT Pub. No.: WO2014/154651
PCT Pub. Date: Oct. 2, 2014

(65) Prior Publication Data
US 2016/0054301 A1   Feb. 25, 2016

(30) Foreign Application Priority Data

Mar. 26, 2013 (FR) .................... 13 52732
Jul. 22, 2013 (FR) .................... 13 57197

(51) Int. Cl.
*G01N 33/50* (2006.01)

(52) U.S. Cl.
CPC ........... *G01N 33/5005* (2013.01); *G01N 2333/70596* (2013.01); *G01N 2400/38* (2013.01); *G01N 2400/40* (2013.01)

(58) Field of Classification Search
CPC .................................. G01N 33/5005
See application file for complete search history.

(56) References Cited

U.S. PATENT DOCUMENTS

| 2009/0239819 A1* | 9/2009 | Wang ............. C12Q 1/04 514/54 |
| 2014/0051097 A1 | 2/2014 | Lanos et al. |
| 2015/0125871 A1 | 5/2015 | Duvet et al. |

FOREIGN PATENT DOCUMENTS

| WO | WO 2011/158016 | 12/2011 |
| WO | WO 2012/143647 | 10/2012 |
| WO | WO 2013/178931 | 12/2013 |

OTHER PUBLICATIONS

Wardenburg et al. PNAS, 2006103(37):13831-13836.*
Dziarski, R., et al., "*Staphylococcus aureus* Peptidoglycan is a Toll-Like Receptor 2 Activator: a Reevaluation," *Infection and Immunity*, Aug. 2005, vol. 73, No. 8, pp. 5212-5216.
Erridge, C., "The capacity of foodstuffs to induce innate immune activation of human monocytes in vitro is dependent on food content of stimulants of Toll-like receptors 2 and 4," British Journal of Nutrition, Jan. 1, 2011, vol. 105, No. 1, pp. 15-23.
Timmerman, C.P., et al., "Induction of Release of Tumor Necrosis Factor from Human Monocytes by Staphylococci and Staphylococcal Peptidoglycans," *Infection and Immunity*, Oct. 1, 1993, vol. 61, No. 10, pp. 4167-4172.
Written Opinion in International Application No. PCT/EP2014/055888, Jun. 17, 2014, pp. 1-6.
Currently pending claims of U.S. Appl. No. 14/110,569, 2015, pp. 1-5.
Final Office Action dated Feb. 1, 2016 in U.S. Appl. No. 14/110,569.
Currently pending claims of U.S. Appl. No. 14/403,600, 2014, pp. 1-8.

* cited by examiner

*Primary Examiner* — Bin Shen
(74) *Attorney, Agent, or Firm* — Blank Rome LLP

(57) ABSTRACT

The present invention relates to a biological method for assaying peptidoglycans (PGN) in a sample, particularly a sample of glucose polymers. The PGN assay includes: a) treating the glucose polymer sample by sonication, heating, and/or alkalizing; b) placing the treated sample or a dilution thereof in contact with a recombinant cell expressing an exogenous TLR2 (toll-like receptor 2) and a reporter gene directly dependent on the signaling pathway associated with the TLR2. The reporter gene codes for a colored or fluorescent protein or for a protein the activity of which is measurable with or without a substrate; c) measuring the reporter gene signal; and d) determining the amount of PGN in the sample using a standard curve of the correlation between the amount or PGN and the strength of the reporter gene signal.

11 Claims, 3 Drawing Sheets

BIOLOGICAL ASSAY OF PEPTIDOGLYCANS

CROSS-REFERENCE TO RELATED APPLICATION

This application is the U.S. national stage application of International Patent Application No. PCT/EP2014/055888, filed Mar. 25, 2014.

FIELD OF THE INVENTION

The present invention relates to assay of peptidoglycans in a sample, in particular a sample of glucose polymers.

CONTEXT OF THE INVENTION

Aseptic inflammatory episodes are major complications observed during treatments using manufactured products for therapeutic purposes (for example: peritoneal dialysis, parenteral nutrition, injection by the venous route). Although some of these inflammatory episodes are connected with a problem of a chemical nature (accidental presence of chemical contaminants or incorrect dosages of certain compounds), most cases result from the presence of contaminants of microbial origin released during the manufacturing processes. It is now clearly established that lipopolysaccharides (LPSs) and peptidoglycans (PGNs) are the main contaminants presenting a high risk of triggering such inflammatory episodes when they are present at trace levels in manufactured products.

The LAL (*Limulus* amebocyte lysate) assay is used routinely by many quality control laboratories for detecting and assaying contamination with LPS. This assay is based on recognition of the endotoxins by a sensing complex extracted from *Limulus* (horseshoe crab) hemolymph.

Other assays also based on the reactivity of extracts of invertebrate hemolymph are currently proposed for detecting PGNs in products for therapeutic use (SLP-Wako, Immunetics). However, these assays have the disadvantage that they are not very specific, since they also react with other molecules of microbial origin, such as β-glucans. Moreover, these methods require purchasing special equipment for this use, which greatly increases the costs and therefore limits access to these assay techniques.

Moreover, LPSs and PGNs have variable structures depending on their bacterial origin, which is responsible for large differences in inflammatory reactivity. That is why it is in addition necessary to express the results of the assays in equivalent units of standard molecules (for example, LPS of *E. coli* in the LAL assay).

Moreover, these molecules are most often present in the form of macromolecular complexes, which affects their solubility and their inflammatory potential. For example, the PGNs are very variable in size and are often aggregated with other molecules of the bacterial wall, such as lipoteichoic acids and lipopeptides.

Thus, "biological" methods have been developed solely to take account of the inflammatory load associated with these molecules. The effector cells of the inflammatory response possess special sensors for recognition of molecular structures specifically produced by infectious agents. These molecules, called PAMPs for pathogen-associated molecular pattern molecules, are essentially recognized by TLRs (Toll-like receptors) and NLRs (Nod-like receptors), whose specificity is related to the molecular structure of the different classes of inflammatory molecules. In contrast to LPS (which is a ligand recognized by type TLR4 receptors), PGN is a ligand recognized by type TLR2 receptors.

In recent years, cellular assays in vitro have been developed to replace the animal models of inflammatory response. Most of these assays are based on the incubation of monocyte cells in the presence of the contaminated products and on back-titration of the production of inflammatory cytokines (TNF-α, IL-1µ, IL-6, IL-8, RANTES). However, assays using primary cells isolated from blood are subject to considerable inter-individual variability of the donors, which may be responsible for experimental bias.

In contrast, the monocyte cell lines give constant responses, which explains why they are generally preferred to primary cells. However, these lines are not completely satisfactory either. For example, the choice of cytokines is often criticized, as most are expressed transiently and their concentration in the culture medium does not always reflect the real load of inflammatory molecules. Since all the monocyte cells express the majority of the TLRs/NLRs, assays based on their use are not selective for one type of contaminant, but will give an overall inflammatory response.

Moreover, the main problem arises from the differences in sensitivity of the cells with respect to the different inflammatory molecules. Thus, the PGNs, TLR2 ligands, are far less reactive than the LPSs, which makes them difficult to detect by these approaches. In fact, the LPSs induce a significant response for concentrations of the order of ng/mL, whereas 100 times higher concentrations of PGN are necessary to obtain a similar response (w/w ratio).

For some years, transfected cell lines have been proposed for replacing the above models in the biological assays for detecting and quantifying the reactivity of inflammatory compounds. These noninflammatory lines (for example: HEK-293) are stably transfected by a gene coding for a specific receptor of a class of inflammatory agonists. They also contain an expression vector for a reporter gene coding for an enzyme (for example, luciferase or alkaline phosphatase), whose synthesis is dependent on activation of the inflammatory receptor. Thus, recognition of a contaminant by the cells expressing the appropriate receptor will trigger the synthesis of the enzyme, production of which will be followed by transformation of its substrate into a colored or luminescent product. As this product is easily quantifiable, this method allows rapid assay of the inflammatory response associated with a type of contaminant.

These cellular models have many advantages: replacement of ELISA assays of cytokines with an enzyme assay, great reproducibility of the assays on account of the stable character of the lines, targeting of certain classes of inflammatory molecules as a function of the receptor expressed, detection of contaminants at very low thresholds.

These cellular models may therefore replace the assays of cytokine response in vitro, as they make it possible to target specifically the inflammatory factors that are agonists of a given TLR or NLR, and quantify the inflammatory response associated with this agonist. For example, cells specifically expressing TLR2 and TLR4 have already been used for detecting contaminants in food products (works of Clett Erridge of the Department of Cardiovascular Sciences of Leicester—UK in *British Journal of Nutrition*, Vol. 105/ issue 01/January 2011, pp 15-23).

Moreover, companies such as InvivoGen now market a wide range of cells of the HEK-293 line (HEK-Blue™) transfected with the various TLR or NRL receptors. These cells contain, as reporter, a gene coding for a secreted form of alkaline phosphatase (SEAP: secreted embryonic alkaline phosphatase), which allows quick and easy colorimetric assay of the response to the inflammatory agonists.

These HEK-Blue™ cells have already been used successfully for detecting the presence of contaminants in concentrated solutions of glucose polymer and their synergistic effect (WO2012/143647). As the aim stated in this application is solely to detect the contaminants that are in a form displaying inflammatory activity, the methods described in this patent application are not suitable for measuring the total amount of PGN contained in the sample. In fact, the soluble PGNs (MM 120 kDa) are those that induce an inflammatory response via the TLR2 receptor. Thus, the PGNs not having a suitable size to be inflammatory or aggregated with other molecules are not detected by the method described in this application.

Thus, there is a constant need to develop alternative methods of assaying total PGN in a sample, in particular a sample of glucose polymers.

SUMMARY OF THE INVENTION

The present invention therefore relates to a biological method for assaying the peptidoglycans in a sample, in particular a sample of glucose polymers.

In particular, the present invention relates to a method of assaying peptidoglycans (PGNs) in a sample of glucose polymer, comprising:
a) treating the sample of glucose polymer by sonication, heating, and/or alkalization;
b) bringing the treated sample or a dilution thereof into contact with a recombinant cell expressing an exogenous TLR2 receptor (Toll-like Receptor 2) and a reporter gene under the direct dependence of the signaling pathway associated with the TLR2 receptor, said reporter gene coding for a colored or fluorescent protein or for a protein whose activity can be measured with or without substrate;
c) measuring the reporter gene signal; and
d) determining the amount of PGN in the sample using a calibration curve of the correspondence between the amount of PGN and the intensity of the reporter gene signal.

Preferably, treating the sample by sonication, heating, and/or alkalization makes it possible to fragment and disintegrate the PGNs contained in the sample, in particular so as to make them capable of activating the TLR2 receptor. In particular, the treatment of the sample makes it possible to generate PGNs predominantly with a size of about 120 kDa.

Preferably, the reporter gene is a secreted alkaline phosphatase. In a preferred embodiment, the cell is a cell of the HEK-Blue™ hTLR2 line.

Preferably, the calibration curve of the correspondence between the amount of PGN and the intensity of the reporter gene signal was prepared with PGNs derived from a bacterium selected from *Staphylococcus aureus, Micrococcus luteus, Bacillus subtilis* and *Alicyclobacillus acidocaldarius*, preferably from *Staphylococcus aureus, Micrococcus luteus*, and *Alicyclobacillus acidocaldarius*. In particular, the method may comprise a preliminary step of preparation of the calibration curve using PGNs derived from a bacterium selected from *Staphylococcus aureus, Micrococcus luteus, Bacillus subtilis* and *Alicyclobacillus acidocaldarius*, preferably from *Staphylococcus aureus, Micrococcus luteus*, and *Alicyclobacillus acidocaldarius*.

Preferably, the sample is diluted, if necessary, so as to generate a signal of the reporter gene corresponding to the linear portion of the calibration curve.

Preferably, the sample is a sample of a solution of icodextrin.

Preferably, the calibration curve of the correspondence between the amount of PGN and the intensity of the reporter gene signal is standardized or calibrated with an internal standard that is an agonist of TLR2, preferably a lipopeptide, in particular PAM$_3$Cys-Ser-(Lys)4 trihydrochloride.

In an alternative embodiment, the calibration curve of the correspondence between the amount of PGN and the intensity of the reporter gene signal was prepared with an internal standard that is an agonist of TLR2, preferably a lipopeptide, in particular PAM$_3$Cys-Ser-(Lys)4 trihydrochloride. In particular, the method may comprise a preliminary step of preparation of the calibration curve using an internal standard that is an agonist of TLR2, preferably a lipopeptide, in particular PAM$_3$Cys-Ser-(Lys)4 trihydrochloride.

The invention further relates to a kit for assaying peptidoglycans (PGNs) in a sample of glucose polymers, comprising:
a recombinant cell expressing an exogenous TLR2 receptor (Toll-like Receptor 2) and a reporter gene under the direct dependence of the signaling pathway associated with the TLR2 receptor, said reporter gene coding for a colored or fluorescent protein or for a protein whose activity can be measured with or without substrate; and
either a calibration curve of the correspondence between the amount of PGN and the intensity of the reporter gene signal, or a PGN standard, preferably derived from a bacterium selected from *Staphylococcus aureus, Micrococcus luteus, Bacillus subtilis* and *Alicyclobacillus acidocaldarius*, preferably from *Staphylococcus aureus, Micrococcus luteus*, and *Alicyclobacillus acidocaldarius*, or an internal standard that is an agonist of TLR2, preferably a lipopeptide, in particular PAM$_3$Cys-Ser-(Lys)4 trihydrochloride;
optionally instructions for use and/or a solution for pretreating the sample.

Preferably, the kit further comprises an internal standard that is an agonist of TLR2, preferably a lipopeptide, in particular PAM$_3$Cys-Ser-(Lys)4 trihydrochloride.

DETAILED DESCRIPTION OF THE INVENTION

The present invention therefore relates to a biological method for assaying the peptidoglycans in a sample, in particular a sample of glucose polymers.

In particular, the present invention relates to a method of assaying peptidoglycans (PGNs) in a sample of glucose polymer, comprising:
a) treating the sample of glucose polymer by sonication, heating, and/or alkalization;
b) bringing the treated sample or a dilution thereof into contact with a recombinant cell expressing an exogenous TLR2 receptor (Toll-like Receptor 2) and a reporter gene under the direct dependence of the signaling pathway associated with the TLR2 receptor, said reporter gene coding for a colored or fluorescent protein or for a protein whose activity can be measured with or without substrate;
c) measuring the reporter gene signal; and
d) determining the amount of PGN in the sample using a calibration curve of the correspondence between the amount of PGN and the intensity of the reporter gene signal.

Preferably, the glucose polymers are intended for peritoneal dialysis, enteral and parenteral nutrition and feeding of neonates. In a preferred embodiment, the glucose polymers that will be tested are icodextrin or maltodextrins. In particular, they may be intended for preparation for peritoneal dialysis. They can be tested at one or more stages of their preparation, and notably at the level of the raw material, in any step in their preparation process, and/or at the level of the end product of the process. They may also be tested as a sample of a solution for peritoneal dialysis.

In a first step of the method, the sample of glucose polymer is treated by sonication, heating, and/or alkalization. The aim of this treatment is to fragment the PGNs and/or disintegrate the PGNs contained or trapped in aggregates, the aim being to generate PGNs capable of interacting with the TLR2 receptors and activating them. As stated above, this treatment should make it possible to disintegrate the PGNs contained or trapped in aggregates and to fragment the PGNs that are too large, notably to generate soluble PGNs with sizes between 30 and 5000 kDa, notably of about 120 kDa. However, the treatment must not affect the capacity of the PGNs for interacting with the TLR2 receptors. It is preferably optimized for maximum release of PGNs capable of interacting with TLR2 and of activating the receptor and for storing a maximum of PGNs already active on TLR2.

In a first embodiment, the treatment of the sample comprises at least one sonication step. Optionally, sonication may take from 30 seconds to 5 minutes, use a power of 20 to 40 kHz and/or comprise one or more sonication cycles, for example from 1 to 5 cycles. In a preferred embodiment, the sample will be treated by sonication for 1 minute at 35 kHz in a single cycle. Optionally, the treatment by sonication may be combined with treatment by heating and/or by alkalization.

In a second embodiment, the treatment of the sample comprises at least one alkalization step. Preferably, the alkalizing agent is NaOH, notably at a concentration between 0.1 and 1 M. Optionally, the duration of the alkalization step may be from 5 minutes to 60 minutes. Optionally, the alkalization step may be carried out at a high temperature, notably a temperature between 20° C. and 80° C., for example at a temperature of 20, 40, 60 or 80° C. Optionally, the treatment by alkalization may be combined with treatment by sonication.

In a second embodiment, the treatment of the sample comprises at least one heating step. Optionally, the duration of the heating step may be from 5 minutes to 60 minutes. Optionally, the heating step may be carried out at a high temperature, notably a temperature between 20° C. and 80° C., for example at a temperature of 20, 40, 60 or 80° C. Optionally, the heating treatment may be combined with treatment by sonication and/or by alkalization.

The methods of sample treatment do not comprise steps of enzymatic treatment, notably by a mutanolysin.

In a subsequent step, the sample and/or dilutions thereof is/are brought into contact with recombinant cells expressing the TLR2 receptor. The cells are qualified as recombinant as they are cells that have been modified by the introduction of a nucleic acid coding for the TLR2 receptor, preferably the human TLR2 receptor, the initial cell not expressing TLR2.

The activity of the TLR2 receptor is detected using a reporter gene that is under the direct dependence of the signaling pathway associated with said receptor. Preferably, this reporter gene codes for a colored or fluorescent protein, or for a protein whose activity can be measured with or without substrate. In particular, the reporter gene codes for an alkaline phosphatase. Notably, the reporter gene may produce a secreted form of alkaline phosphatase (SEAP: secreted embryonic alkaline phosphatase), whose synthesis is under the direct dependence of the signaling pathway associated with TLR2.

In a preferred embodiment, the cell line used is a HEK-10 Blue™ line (marketed by the company InvivoGen), modified by stable transfection with vectors coding for human TLR2: the HEK-Blue™ hTLR2 line. However, it should be noted that a person skilled in the art may also use other lines commercially (Imgenex) or he can prepare them.

When the cell is HEK-Blue™ hTLR2, the cell is preferably used at a density of about 50 000 cells/well for a 96-well plate.

In a particular embodiment, the sample of glucose polymers or a dilution thereof has a concentration of glucose polymers from 5 to 50 mg/mL, preferably between 5 and 10, 20, 30 or 40 mg/mL. In the preferred embodiment, the sample of glucose polymers or a dilution thereof has a concentration of glucose polymers of about 37.5 mg/mL.

In another particular embodiment, the sample of glucose polymers or a dilution thereof has a maximum concentration of glucose polymer of 3.75% (weight/volume), preferably 3%.

For example, the samples are prepared so as to have a concentration of glucose polymer of 3.75% (weight/volume), preferably 3%, and the samples are submitted to the method of assay according to the present invention, assaying the sample as well as 1/10, 1/100 and 1/1000 dilutions.

Preferably, bringing the sample of glucose polymers or a dilution thereof into contact with the cells takes about 5 to 48 h, preferably from 10 to 36 h, more preferably from 16 to 24 h.

Next, the method comprises measurement of the reporter gene signal.

In a preferred embodiment using the HEK-Blue™ hTLR2 line, the signal is a measure of the activity of alkaline phosphatase. Preferably, the enzymatic reaction is carried out using a 1:3 ratio of medium to be assayed to SEAP reagent (for example 50 μL of medium and 150 μL of SEAP reagent). Moreover, a reaction time of at least 60 minutes will be preferred.

Finally, the amount of PGN in the sample is determined using a calibration curve of the correspondence between the amount of PGN and the intensity of the reporter gene signal.

This curve is preferably obtained with the same cells, in the same conditions, with increasing doses of PGNs, in particular PGN standards.

The PGN standard may be any PGN of bacterial origin. For example, the PGNs may be derived from the following microorganisms: *Staphylococcus aureus, Micrococcus luteus, Escherichia coli, Bacillus subtilis* and *Alicyclobacillus acidocaldarius*. In particular, the standards used are purified and partially digested PGNs. Such standards are available commercially (Invitrogen, Catalog # tlrl-pgnec or tlrl-pgnek from *E coli*; Catalog # tlrl-pgnb2 from *B subtilis*; Catalog # tlrl-pgnsa from *S aureus*) (Wako Pure Chemical, Catalog #162-18101 from *M luteus*).

The PGN standard is preferably calibrated using an internal standard that is an agonist of TLR2, so as to express the results in equivalent units of active PGN. The internal standard may be a lipopeptide, preferably synthetic, in particular $PAM_3Cys$-Ser-(Lys)4 trihydrochloride (Pam3 (cys), PAM or Pam signifying palmitic acid) (see FIG. 5). Thus, the calibration curve of the correspondence between the amount of PGN and the intensity of the reporter gene signal is preferably standardized or calibrated with an internal standard that is an agonist of TLR2, preferably a lipopeptide, in particular $PAM_3Cys$-Ser-(Lys)4 trihydrochloride. This internal standard is preferably synthetic or with a well-defined structure/composition. The calibration or standardization is carried out by comparing the slopes of the linear portions of each dose-response curve and calculating a correction factor allowing the curve obtained with the calibration standard and that of the PGN standard to be superimposed.

For example, the calibration curve may be obtained using concentrations of PGNs from 0.001 to 1000 ng/mL, notably from 0.01 to 100 ng/mL.

This calibration curve may be obtained either with PGNs only, or with a solution of glucose polymer to which defined quantities of PGNs have been added. Notably, the solution of glucose polymer used may comprise 3.75% (weight/volume) of glucose polymer, preferably 3%.

This curve of the correspondence between the amount of PGN and the intensity of the reporter gene signal can also be obtained with an internal standard that is an agonist of TLR2, preferably a lipopeptide, in particular PAM$_3$Cys-Ser-(Lys)4 trihydrochloride, notably with the same cells, in the same conditions, with increasing doses of TLR2 agonist internal standard. This internal standard is preferably synthetic or with a well-defined structure/composition. Just as for PGN, it can be obtained in the absence of or, preferably, in the presence of glucose polymer.

Typically, the calibration curve is a classical curve of cellular response of the sigmoid type (FIG. 1).

part (A) corresponds to the responses obtained with low concentrations of PGN, below those giving effective activation of TLR2. This nonlinear zone therefore corresponds to the limit of detection of the method. So as to include the variability of the method, this detection threshold is estimated at three times the value of the background noise (response obtained in the absence of a stimulus);

part (B) is the most interesting as a linear response is observed. This zone with effective response makes it possible to determine a direct relation between the cellular response and the PGN level. This is therefore the assay zone;

part (C) corresponds to saturation of the cellular response in the presence of excessive concentrations of PGN. There is in fact saturation of the TLR2 receptors.

The linear part of the calibration curve is considered; this part corresponds to a zone (part B) in which the amount of PGN is directly proportional to the reporter gene signal.

In the case of samples likely to be heavily contaminated with PGN, it will be necessary to perform several series dilutions so as to still be located in the zone of linearity. Otherwise, low concentrations of PGN require a step of concentration of the sample if we wish to increase the sensitivity of the assay.

Optionally, the method further comprises an assay with a control cell that does not express TLR2, more generally that does not express an innate immunity receptor. For example, the HEK-Blue™ Null2 line may be used. This is a control line, use of which is useful for verifying that the sample of glucose polymers does not induce production of the enzyme by an intrinsic mechanism.

The present invention also relates to a kit for assaying peptidoglycans (PGNs) in a sample of glucose polymers, said kit comprising:

a recombinant cell expressing an exogenous TLR2 receptor (Toll-like Receptor 2) and a reporter gene under the direct dependence of the signaling pathway associated with the TLR2 receptor, said reporter gene coding for a colored or fluorescent protein or for a protein whose activity can be measured with or without substrate. Notably, the cell is preferably the HEK-Blue™ hTLR2 line. As negative control, the kit may also comprise a cell not expressing an innate immunity receptor, for example the HEK-Blue™ Null2 line.

either a calibration curve of the correspondence between the amount of PGN and the intensity of the reporter gene signal, or a calibrated PGN standard, preferably derived from a bacterium selected from *Staphylococcus aureus, Micrococcus luteus, Escherichia coli,* and *Alicyclobacillus acidocaldarius*, preferably *Staphylococcus aureus*, or an internal standard that is an agonist of TLR2, preferably a lipopeptide, in particular PAM$_3$Cys-Ser-(Lys)4 trihydrochloride. Optionally, the kit may comprise both, i.e. a calibration curve as well as a calibrated PGN standard derived from the same microorganism as that used for preparing this calibration curve.

optionally instructions for use, a solution for pretreating the sample, the reagents to be used for measuring the response of the reporter gene, microplates, etc.

Preferably, the kit further comprises an internal standard that is an agonist of TLR2, preferably a lipopeptide, in particular PAM$_3$Cys-Ser-(Lys)4 trihydrochloride.

EXAMPLES

The assay is based on the specific recognition of PGNs by a line expressing the TLR2 receptor and on the production of an enzyme activity measurable via activation of the signaling pathway associated with TLR2.

Cellular Material

For the experiments relating to this assay, two lines are used:

HEK-Blue™ hTLR2 line (HEK-TLR2): specific response for the TLR2 ligands, with strong reactivity for the soluble PGNs.

HEK-Blue™ Null2 line (HEK-Null): nonspecific response connected with a cytotoxic effect of the sample.

The cells are cultured according to the supplier's recommendations (InvivoGen). At 75% confluence, the cells are resuspended at a density of 0.28×10$^6$ cells/mL. Before stimulation, 180 µL of the cellular suspension is distributed in the culture wells (96-well plate), or 50 000 cells/well. The cells are then stimulated for 24 h by adding 20 µL of the samples of glucose polymer at 37.5% (weight/volume) (i.e. a final dilution of the samples at 3.75%). After 24 h of stimulation, the cellular response is measured by quantification of the enzyme activity produced.

1—Establishment of the Dose-Response Curve

Figure 1:
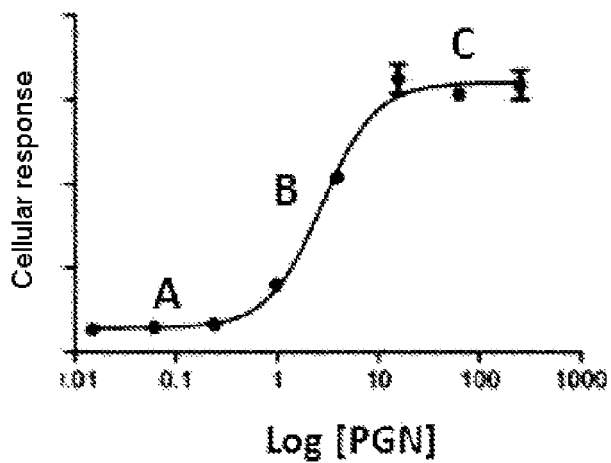
FIG. 1: Theoretical curve of the cellular response as a function of increasing concentrations of PGN.
Figure 2:
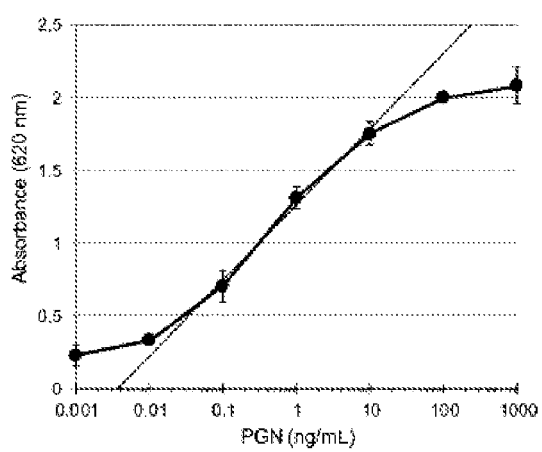
FIG. 2: Calibration curve of the cellular response as a function of the PGN level of *S. aureus* obtained with the HEK-Blue™-hTLR2 cells.

A dose-response curve was constructed by diluting different amounts of PGN standard of *S. aureus* (FIG. 2) in a solution of uncontaminated icodextrin prepared at 37.5% (weight/volume) (FIG. 2).

The result is a classical curve of cellular response of the sigmoid type.

part (A) corresponds to the responses obtained with low concentrations of PGN, below those giving effective activation of TLR2. This nonlinear zone therefore corresponds to the limit of detection of the method.

part (B) is the most interesting as a linear response is observed. This zone of effective response makes it possible to determine a direct relation between the cellular response and the PGN level. This is therefore the assay zone.

part (C) corresponds to saturation of the cellular response in the presence of excessive concentrations of PGN. There is in fact saturation of the TLR2 receptors.

The standard curve of response of the HEK-TLR2 cells to the PGN of *S. aureus* has a zone of linearity for concentrations between 0.07 and 10 ng/mL (i.e. between 2 and 267 ng/g of icodextrin).

2—Establishment of the Calibration Curve for Biological Assay of PGNs with an Internal Standard The dose-response curves were constructed by diluting the PGNs of different bacterial species in a solution of uncontaminated maltodextrin (referenced P-11.11) prepared at 37.5% (weight/volume). The PGNs assayed are extracted from *Staphylococcus aureus* (Sigma, Cat No 77140), *Micrococcus luteus* (Sigma, Cat No 53243), *Bacillus subtilis* (InvivoGen, # tlrl-pgnb2), and *Alicyclobacillus acidocaldarius* (personal preparation).

Figure 3:
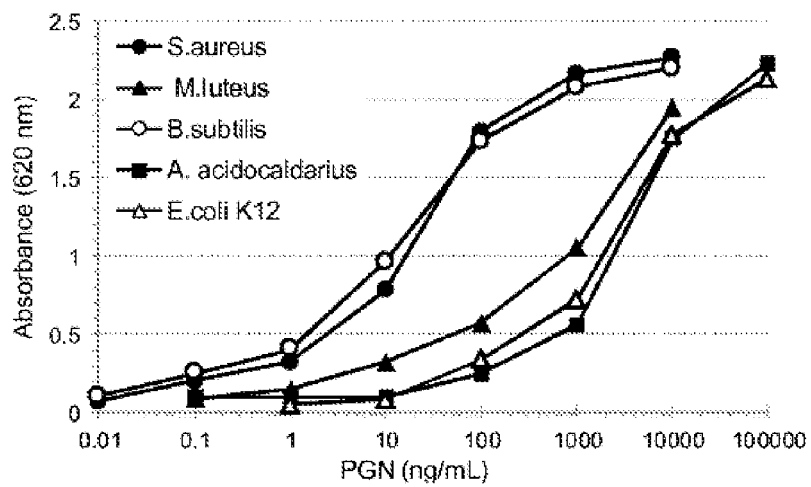
FIG. 3: Response of the HEK-Blue™-hTLR2 cells as a function of increasing concentrations of PGN from different bacterial species.

The curves obtained are classical curves of the responses observed in the assays performed with a cellular material (bioassay) (FIG. 3). The absorbance values below 0.2 are evidence of PGN concentrations that are too low to induce a cellular response, whereas values above 2 show a plateau effect connected with saturation of the TLR2 receptors. Consequently, only the zone between these two limit values of absorbance allows correlation of the production of SEAP with the amount of PGN present in the samples.

The responses observed show a large variability in the cellular reactivity associated with each type of PGN. In fact, the concentrations giving a response equal to 50% of the maximum response (EC50) are ~20 ng/mL for the PGNs of *S. aureus* and *B. subtilis,* 1500 ng/mL for *M. luteus*, and more than 2000 ng/mL for those extracted from *A. acidocaldarius* and *E. coli* K12.

However, these differences were expected, since the PGNs have different structures depending on their bacterial origin, which is responsible for large variations in inflammatory reactivity. These observations emphasize the importance of defining an internal standard so as to be able to express the results in equivalent units of PGN.

Another factor likely to alter the response of the HEK-TLR2 cells is the size of the PGNs, which will influence their solubility and reactivity with respect to TLR2. Thus, the procedure for purification of these macromolecules may have a considerable influence on the response of the cells, since the conditions of extraction could alter the size of the PGNs, or even cause partial degradation. To test this hypothesis, the assays were reproduced with 3 separate batches of PGNs extracted from *S. aureus:* 2 Sigma batches (Cat No 77140: batch 1, 0001442777; batch 2, BCBH7886V) and 1 InvivoGen batch (# tlrl-pgnsa).

Figure 4:
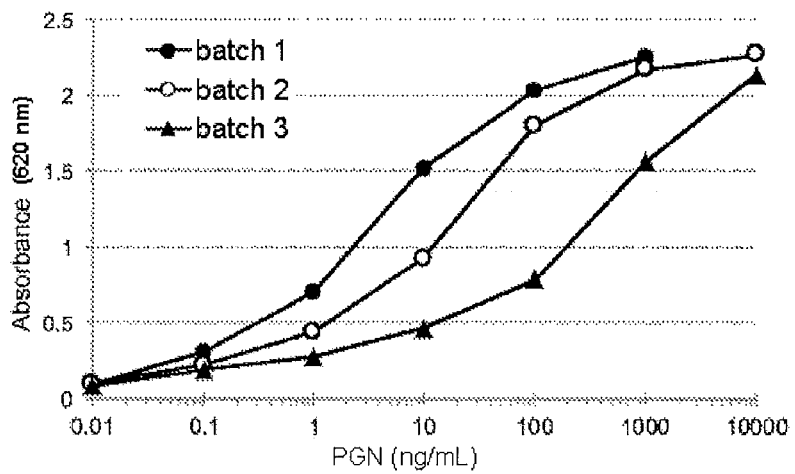
FIG. 4: Response of the HEK-Blue™-hTLR2 cells as a function of increasing concentrations of PGN of *S. aureus* obtained from different batches.

The results show variability of reactivity between the three batches (FIG. 4). In fact, the EC50 values are 4, 20 and 400 ng/mL respectively for the three batches. These data indicate that there is a risk that PGNs extracted from the same bacterial species might show differences in reactivity, even if the batches were obtained from the same supplier and were extracted beforehand by the same procedure. It therefore seems necessary to introduce an internal standard for the calibration curve, so as to avoid errors relating to the variability of the PGNs and to express the results as amount of "active" PGN.

Figure 5:
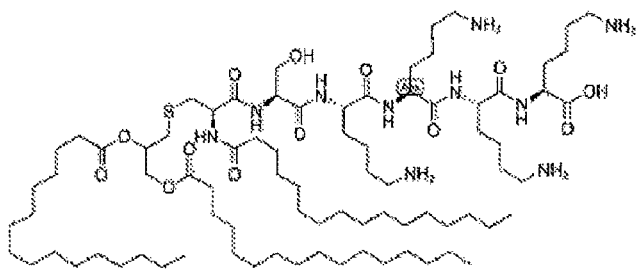
FIG. 5: Structure of PAM$_3$Cys-Ser-(Lys)4 trihydrochloride (PAM3(cys)).

PAM$_3$Cys-Ser-(Lys)4 trihydrochloride (PAM3(cys); FIG. 5) is a triacylated synthetic lipopeptide that mimics the structure of the bacterial lipopeptides and acts as a strong agonist of TLR2. Being of homogeneous structure, it is often used as positive control for calibrating the responses of the cells expressing the TLR2 receptor.

Figure 6:
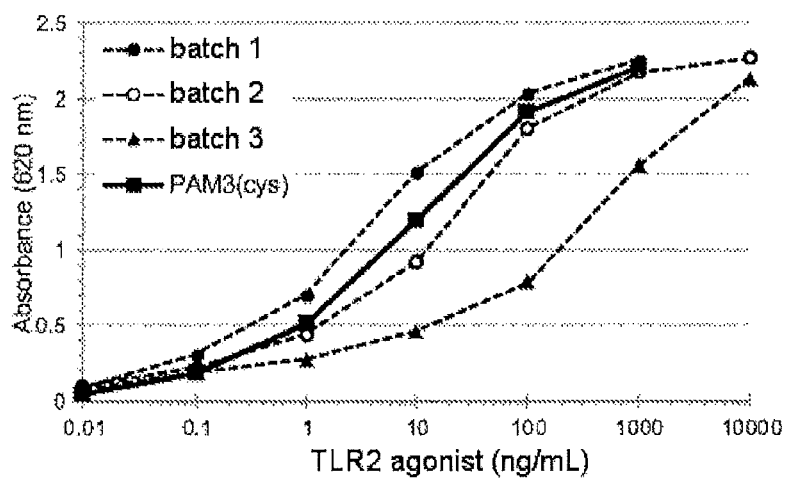
FIG. 6: Comparison of the responses induced by the PGNs of *S. aureus* and PAM3(cys) in the HEK-Blue™-hTLR2 cells.

The experiments were therefore reproduced replacing PGN with PAM3(cys) in our tests. As expected, the HEK-TLR2 cells show strong reactivity with respect to this compound. Moreover, the shape of the dose-response curve is similar to those obtained in the presence of PGN, with EC50 estimated at 10 ng/mL (FIG. 6). These results indicate that PAM3(cys) induces responses equivalent to those of the most reactive PGNs, but in contrast to the latter, it does not display structural variability. Consequently, this synthetic lipopeptide can be used for calibrating the batches of PGN and for establishing a standardized calibration curve, which will allow the results to be formulated in amounts of "active" PGN, i.e. in amounts of PGN giving TLR2 responses identical to those obtained with the same amounts of PAM3 (cys).

Figure 7:
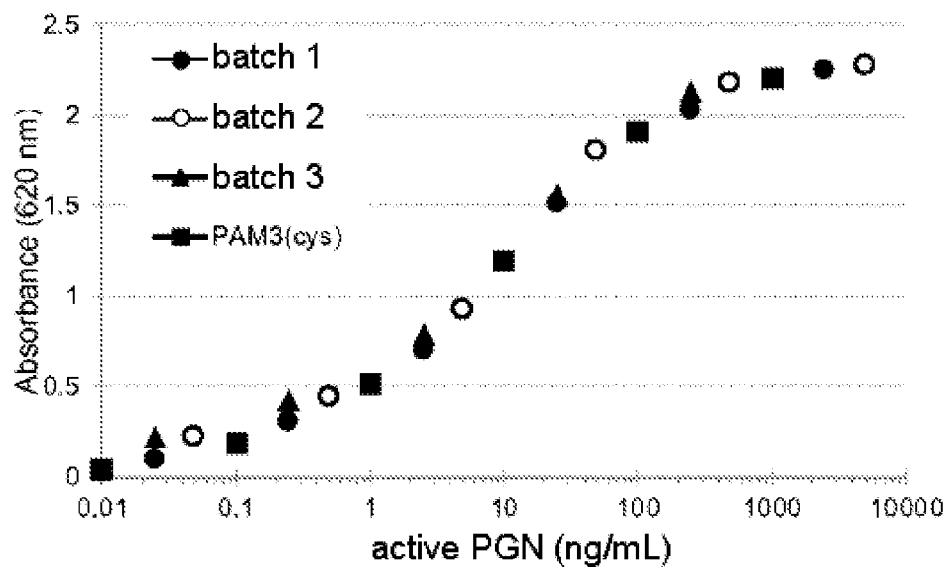
FIG. 7: Response of the HEK-Blue™-hTLR2 cells as a function of the corrected PGN concentrations.

Each batch of PGN is calibrated relative to PAM3(cys) by comparing the slopes of the linear portions of each dose-response curve, and calculating a correction factor for superimposing the curves of the PGNs on that of PAM3(cys). In the example presented in FIG. 6, the correction factors were estimated at 0.4, 2 and 40 for batches 1, 2 and 3, respectively. This means that 2.5 times less PGN from batch 1 is required for obtaining responses identical to those induced by PAM3(cys), but 2 times more PGN from batch 2 and 40 times more PGN from batch 3. After correcting the raw quantities of PGN, it can be seen that all the points are aligned on one and the same curve, which can be superimposed on that obtained with PAM3(cys) (FIG. 7). Consequently, using the internal standard makes it possible to obtain corrected concentrations for all the batches of PGN and establish a dose-response curve calibrated for active PGN.

Figure 8:
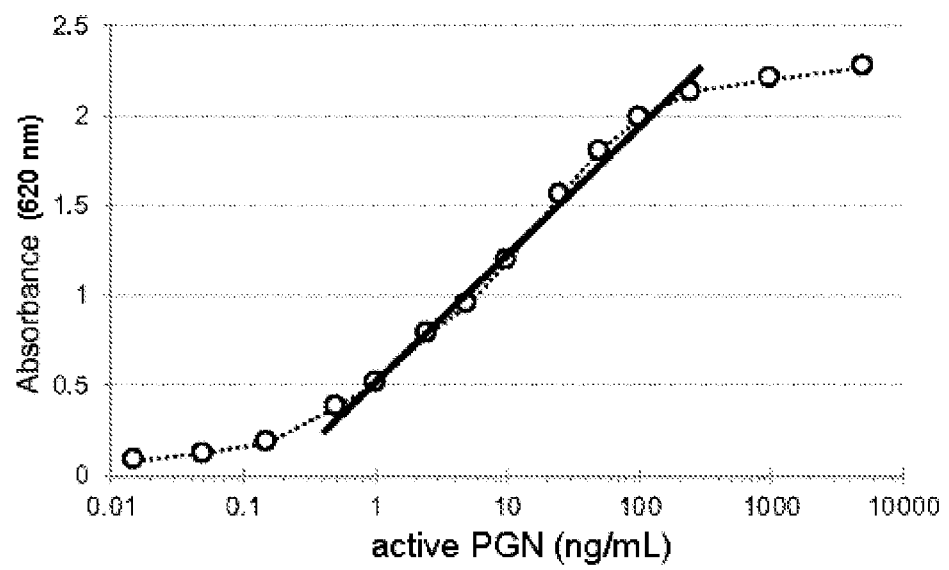
FIG. 8: Calibration curve of the response of the HEK-Blue™-hTLR2 cells as a function of the corrected active PGN concentrations.

By applying this method, the standard curve of response of the HEK-TLR2 cells has a zone of linearity for concentrations of active PGN between 0.5 and 200 ng/mL (FIG. 8), or between 13 and 5400 ng/g of glucose polymers.

The invention claimed is:

1. A method of assaying a level of peptidoglycan (PGN) contaminants in a sample of glucose polymer manufactured for therapeutic purposes, comprising:

obtaining a sample of the glucose polymer manufactured for therapeutic purposes;

treating the glucose polymer sample by sonication, heating, and/or alkalization to fragment and disintegrate the PGN contaminants;

contacting the treated sample or a dilution thereof with a reporter gene expressing cell line, wherein the reporter gene expressing cell line is a recombinant cell line encoding an exogenous TLR2 receptor (Toll-like Receptor 2) and a reporter gene dependent on a signaling pathway associated with the TLR2 receptor, the reporter gene coding for a colored or fluorescent protein or for a protein whose activity can be measured with or without a substrate;

establishing a calibration curve with a PGN standard and the reporter gene expressing cell line; and measuring the reporter gene signal relative to the calibration curve, thereby quantitating a level of contamination in the glucose polymer sample.

2. The method of claim 1, wherein the glucose polymer sample has a concentration of glucose polymers ranging from 5 mg/ml to 50 mg/ml.

3. The method of claim 1, wherein the glucose polymer sample is a solution of maltodextrins.

4. The method of claim 1, wherein said reporter gene is a secreted alkaline phosphatase.

5. The method of claim 1, wherein the cell is a stably transformed HEK-293 cell line expressing a human TLR2.

6. The method of claim 1, wherein the calibration curve is established with a PGN standard prepared with PGNs derived from a bacterium selected from *Staphylococcus aureus, Escherichia coli, Micrococcus luteus, Bacillus subtilis* and *Alicyclobacillus acidocaldarius.*

7. The method of claim 6, wherein the PGN standard is a purified and partially digested PGN.

8. The method of claim 1, wherein the sample is diluted to generate a signal of the reporter gene corresponding to a linear portion of the calibration curve.

9. The method of claim 1, wherein the glucose polymer sample is a solution of icodextrin.

10. The method of claim 1 wherein the PGN standard of the calibration curve is a lipopeptide agonist of TLR2.

11. The method of claim 10, wherein the lipopeptide is a $PAM_3Cys\text{-}Ser\text{-}(Lys)_4$ trihydrochloride.

* * * * *